United States Patent [19]

Garfinkel

[11] 4,384,854
[45] May 24, 1983

[54] ANTERIOR SPLINT

[76] Inventor: Leonard M. Garfinkel, 1559 NE. 164 St., North Miami Beach, Fla. 33162

[21] Appl. No.: 312,872

[22] Filed: Oct. 19, 1981

[51] Int. Cl.³ .............................................. A61C 5/00
[52] U.S. Cl. .................................... 433/215; 433/148
[58] Field of Search ............... 433/172, 229, 215, 225, 433/148, 149; 128/89 A

[56] References Cited

U.S. PATENT DOCUMENTS 4,318,694  3/1982  Klein ..................................... 433/18

Primary Examiner—Robert Peshock
Attorney, Agent, or Firm—Barry L. Haley

[57] ABSTRACT

An improved anterior splint that enhances fitting a wire mesh strip to the lingual surfaces of the teeth regardless of tooth crowding, for enhanced bonding, and adds increased labial stability to prevent labial tooth movement that can act after installation to peel away the wire mesh from the lingual surface. One or more small elongated tabs, interproximally disposed, are provided that are initially employed to manipulate and fit the wire mesh along the lingual teeth to be stabilized. Each tab is sized and fastened to the wire mesh to permit the dentist to pull labially on the tab, forcing the wire mesh into interproximal spaces, against the lingual surfaces, in spite of crowding. After the fitting is completed, the wire mesh and the tabs are bonded to the teeth, lingually and interproximally. Excess tab, projecting in front of the teeth is removed, presenting an aesthetic pleasing view.

10 Claims, 7 Drawing Figures

ANTERIOR SPLINT

BACKGROUND OF THE INVENTION

A unitary wire mesh strip, bonded to lingual tooth surfaces, has been employed as an anterior splint to stabilize one or more loose teeth. Such strips are disposed on the lingual surfaces for aesthetic purposes. Because of the wire mesh strip location and the small working space, proper installation of the wire mesh has proven difficult. The dentist has had to manipulate the wire mesh into crowded, irregularly shaped interproximal spaces. The failure to obtain deep interproximal tucking of the wire mesh results in a less durable anterior splint. The second problem with the wire mesh strip splint is that labial movement of the loose tooth often causes peeling away from the bonded mesh, since the mesh strip bonding to the tooth is perpendicular to anterior-posterior movement of the tooth.

The invention described herein overcomes the problems discussed above, both as to installation and permanent disposition. With the present invention the dentist can tuck the mesh deep into an interproximal space by pulling labially on the mesh. Better overall fit of the mesh is achieved by allowing tucking and stretching of the mesh during installation by labial pulling from two different adjacent interproximal spaces. After proper adaptation and fit of the mesh is achieved, each tab is permanently bonded in an interproximal space, and the excess tab removed. The tab then acts as a labial stabilizer for the tooth to prevent anterior-posterior movement that would cause peeling.

SUMMARY OF THE INVENTION

The purpose of the invention is to provide an improved anterior splint that stabilizes one or more loose teeth with a wire mesh strip employing one or more tabs that facilitate installation and enhance ultimate stability. The crux of the invention is based on a thin but durable rectangular tab the length of which is initially longer than the anterior-posterior dimension of the tooth. One end of the tab may be enlarged in a wedge-shape and has a lateral, thin aperture near the wedged end for fastening to the wire mesh. The thickness of the tab is such as to fit firmly but moveably in the interproximal space between adjacent teeth.

One or more tabs are employed in conjunction with the wire mesh strip that comprises the anterior splint, adhesively mounted as a unitary strip across the lingual surfaces of the anterior teeth. Each tab can be labially pulled, tucking the wire mesh deeply in the interproximal spaces, forcing the wire mesh into greater surface contact with each tooth surface, in spite of crowding of the teeth.

Once the wire mesh has been properly fitted by labial manipulation of the tabs by the dentist, the wire mesh and tabs are bonded to the teeth. Each tab is sandwiched by adhesive bonding layers interproximally. Thus each tab acts as an anchor to prevent anterior-posterior movement of the loose teeth. Peeling is prevented because the tabs are fastened to the wire mesh, and in addition provide a bonded plane that is now parallel to the anterior-posterior movement of the teeth being splinted.

Once the splint is permanently installed, the excess portions of the tabs extending beyond the labial surfaces are removed, leaving a pleasing aesthetic appearance of the teeth.

After the initial fitting is achieved, the entire splint and tabs are removed. The lingual and interproximal surfaces of the teeth are prepared for bonding using conventional technics such as acid etching. Minimal interproximal stripping should be employed.

It is an object of this invention to provide a device that greatly facilitates the adaptation and installation of an anterior splint, while simultaneously enhancing the ultimate stabilization of the teeth and the durability of the splint.

It is another object of this invention to provide an improved anterior splint that is easier to install, more durable once installed, and that does not detract from the aesthetic appearance of the teeth.

And yet another object of this invention is to provide an anterior splint using a mesh-like strip and a strip anchor that can be easily but deeply tucked into interproximal spaces during installation, and that prevents anterior-posterior movement of the teeth, preventing peeling away of the mesh-like strip from the tooth surface.

PREFERRED EMBODIMENT

Figure 1:
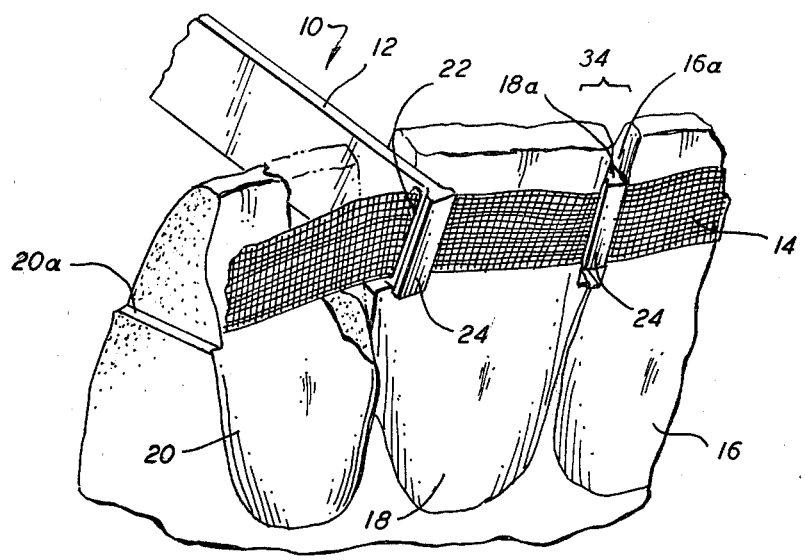
FIG. 1 shows a fragmentary perspective view of lingual surfaces of anterior teeth during installation of the present invention.
Figure 2:
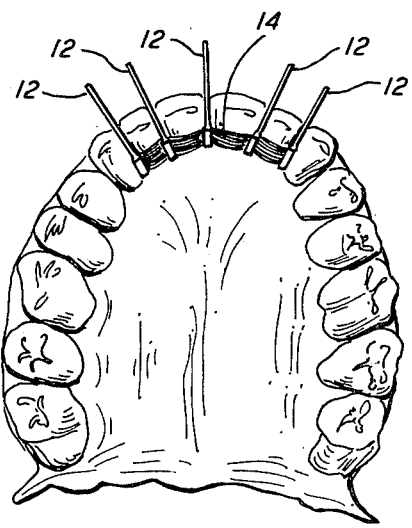
FIG. 2 shows a top plan view of anterior teeth and the present invention during installation.
Figure 3:
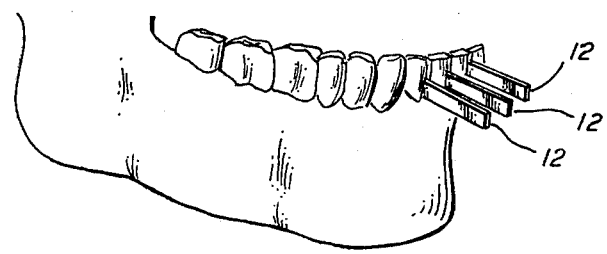
FIG. 3 shows a side elevational view of anterior teeth and the present invention during installation.

Referring now to the drawings and specifically FIGS. 1, 2 and 3, the present invention is shown generally at 10, comprised of a sturdy plastic tab 12 which has a thin lateral aperture 22 disposed at one end, shown on the lingual side of anterior teeth 16, 18 and 20. The device 10, as shown, is represented during installation of the anterior splint.

The anterior splint is comprised of a wire mesh strip 14 which is unitary in construction and, in the preferred embodiment, has minimal memory. The wire mesh strip 14 is threaded through the aperture 22 in each of the tabs 12 which during installation, extend well beyond the labial surfaces of the anterior teeth. Additionally the teeth may be prepared by stripping, indicated by the thin ledge 20a on anterior tooth 20. This provides for more facility in the inserting of the tabs 12, if necessary, due to excessive crowding, but in any event is a very thin space. Each of the tabs 12 has a wedge-like end 24 which aids in achieving a deep tuck of the wire mesh strip 14 into the interproximal spaces (such as space 34 between tooth walls 16a and 18b as an example).

As shown in FIG. 2 and FIG. 3, the tabs project well beyond the labial surfaces of the teeth. These portions of the tabs are grasped by the dentist and pulled labially, thereby both stretching the mesh strip 14 and pulling portions of the mesh strip deep into the interproximal spaces. Because the wire mesh strip has minimal memory, after the device has been properly fitted and adapted to the particular anterior teeth to be splinted, the entire device, both mesh strip and tabs can be removed.

The teeth can then be prepared for bonding with a suitable adhesive by acid etching and stripping, if additional stripping is necessary. Once the teeth are ready to receive the adhesive, the entire device is then reinstalled, after the adhesive has been applied to the interproximal and lingual surface portions concerned. The tabs 12 receive adhesive on both sides of the tab forming an adhesive sandwich that engages both the tab surface walls and adjacent teeth walls in the interproximal spaces. The tabs, if necessary, can be painted with a primer, the job of which, is to enhance the adhesion between the bonding material and tab. During the final installation, the tabs may be firmly secured by the dentist while the adhesive or bonding material sets quickly insuring a tight, perfect fit of the splint.

Figure 4:
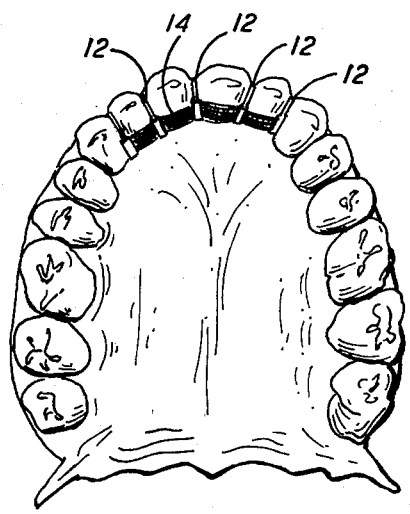
FIG. 4 shows the top plan view of FIG. 2 with the present invention permanently installed.

Referring now to FIG. 4, the anterior splint is shown after the excessive portions of the tabs 12 have been cut off as close to the labial interproximal surfaces of the teeth as possible to prevent being visible from a front view of the teeth. As shown in FIG. 4, the anterior splint is permanently installed.

Figure 5:
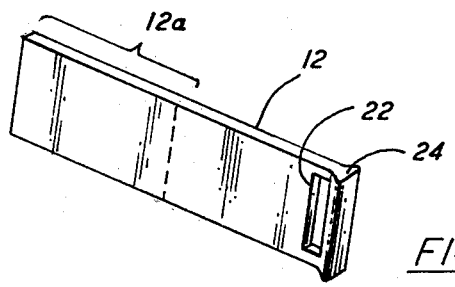
FIG. 5 shows a perspective view of the anchoring tab used in the present invention.

FIG. 5 shows a tab constructed according to the preferred embodiment, including excess portion 12a which is ultimately removed. The tab 12 includes a lateral, thin aperture 22 that receives the wire mesh strip as discussed above. The tab end nearer the aperture 22 may also include an enlarged wedge-shaped end tip 24 that aids in achieving proper contact between the wire mesh strip and surface areas of the teeth in the interproximal spaces.

Figure 6A:
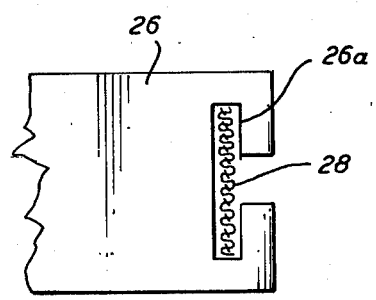
FIGS. 6A and 6B show alternate embodiments of the tab shown in FIG. 5.
Figure 6B:
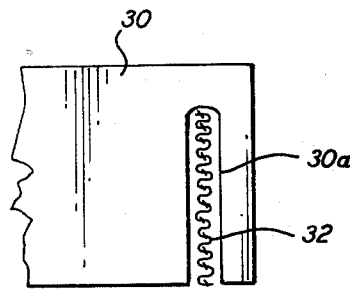

Other modifications of the tab may be utilized to provide the fastening between the tab and the wire mesh strip. Examples of these modifications are shown in FIGS. 6A and 6B. FIG. 6A shows tab 26 having a partially closed aperture 26a that receives wire mesh strip 28. FIG. 6B shows tab 30 having an open recessed portion 30a that receives a wire mesh screen 32. The important consideration in fastening the tab to the wire mesh strip is that the fastening will allow for a pulling force on the wire mesh strip when the tab is pulled labially during installation and will not separate from the wire mesh strip. Also that the tabs can slide along the wire mesh, allowing for varying size teeth and interproximal spaces is another important consideration.

Although in the preferred embodiment the anterior splint strip shown is constructed of a wire mesh, a more or less flexible mesh with a different memory could be employed. Also the tab is shown constructed of a suitable polycarbonate material but could be constructed of other materials. The adhesive and bonding materials employed are conventional.

It can be appreciated from FIG. 4 that, once installed, the anterior splint including the tabs are, for all practical purposes, not visible when the teeth are viewed from the front. Thus the anterior splint provided in the present invention does not in any way detract from the overall aesthetic appearance of the teeth.

It can also be appreciated from FIG. 4 that the remaining tab portions, permanently installed, act in conjunction with the wire mesh strip to prevent anterior-posterior motion of the tooth, thereby preventing peeling of the wire mesh strip from the lingual surfaces of the teeth as has occurred in the prior art. It can also be appreciated (when viewing FIG. 2) that the wire mesh strip can be much more easily manipulated to greater depths in the interproximal regions between the teeth during installation regardless of crowding or the irregular disposition of the particular anterior teeth.

What I claim is:

1. An anterior splint anchor for improving the installation and stability of an anterior splint for anterior teeth, said anterior splint including a unitary, deformable strip bonded to two or more teeth, along the lingual sides of said teeth, said anchor comprising:
    an elongated, firm anchoring member, sized in length to extend from the lingual sides of adjacent teeth sufficiently beyond the labial sides of said teeth to permit grasping, said thickness being sized to permit interproximal disposition and snug engagement with adjacent teeth;
    means for permanently mounting said anchoring member interproximally between adjacent teeth affixed to said anchoring member; and
    means disposed at or near one end of said anchoring member for coupling said flat strip to said anchoring member whereby said anchoring member is pulled labially during installation of said splint, forcing said flat strip into the interproximal spaces of said teeth, and said anchoring member is permanently mounted interproximally between adjacent teeth, the excess portion of said anchoring member extending in front of said teeth being removed, said anchoring member when permanently mounted enhancing labial stability of said teeth.

2. An anterior splint anchor as in claim 1, including:
    tooth bonding coating applied to said anchoring member on each side of said anchoring member, bonding said anchoring member interproximally between adjacent teeth.

3. An anterior splint anchor as in claim 1, wherein:
    said means for coupling said strip to said anchoring member includes a lateral aperture in said anchoring member near one end of said anchoring member, said strip being disposed through said anchoring member aperture.

4. An anchor for an anterior splint as in claim 1, including:
    means disposed at one end of said tab near said anchoring member strip coupling means to aid in guiding strip portions during labial insertion onto interproximal surface portions of said teeth.

5. An anchor for an anterior splint as in claim 4, wherein:
    said means for aiding said interproximal strip insertion is a wedge-shaped end tip integrally formed on said anchoring member end, tapered to narrow in the direction of the main body of said strip.

6. An anchor for an anterior splint as in claim 5, wherein:
    said strip coupling means is a lateral, substantially rectangular tab aperture disposed near said wedge-shaped anchoring member end tip.

7. An anchor for an anterior splint as in claim 1, wherein:
    said anchoring member is constructed of a material such as polycarbonate, or other material capable of adhesing to the bonding or filling material previously refered to and is shaped substantially as an elongated rectangle.

8. An improved anterior splint as in claim 1, wherein:
    said anchoring member is substantially flat, and is rectangular in cross section.

9. The method of using a firm then elongated anchoring member as an anterior splint anchor, said anterior splint including a then deformable strip bonded to portions of the lingual surfaces of two or more adjacent teeth, said method comprising the steps of:

(a) attaching one end of said anchoring member to said anterior splint strip;

(b) disposing said anchoring member in the interproximal space in a labial direction between adjacent teeth; and (c) affixing said anchoring member to interproximal surface protions of said adjacent teeth.

10. The method of using a anchoring member as in claim 9, including the step of:

(d) pulling on said anchoring member labially before affixing said anchoring member to said teeth, forcing portions of said strip into contact with interproximal surface portions of adjacent teeth.

* * * * *